United States Patent [19]

Metzner et al.

[11] 4,337,093

[45] Jun. 29, 1982

[54] WOOD PRESERVING COMPOSITION AND METHOD OF USING SAME

[75] Inventors: Wolfgang Metzner, Krefeld; Hubert Koddebusch, Moers-Vinn, both of Fed. Rep. of Germany; Gerswid Poetter, deceased, late of Duesseldorf, Fed. Rép. of Germany, by Ursula Seeholzer, heiress

[73] Assignee: Deutsche Solvay Werke GmbH, Solingen, Fed. Rep. of Germany

[21] Appl. No.: 165,791

[22] Filed: Jul. 3, 1980

[30] Foreign Application Priority Data

Jul. 6, 1979 [DE] Fed. Rep. of Germany ....... 2927349

[51] Int. Cl.$^3$ ............................................. C09D 5/14
[52] U.S. Cl. .............................. 106/18.33; 106/18.31; 106/18.34; 106/18.35; 424/321
[58] Field of Search ............... 424/321; 260/49.5 QA; 564/79; 106/18.33, 18.34, 18.35

[56] References Cited

U.S. PATENT DOCUMENTS

| | | | |
|---|---|---|---|
| 2,769,006 | 10/1956 | Kalberg | 106/17 |
| 2,966,440 | 12/1960 | Gerolt | 106/16 |
| 3,386,951 | 6/1968 | Pauli et al. | 424/321 |
| 3,492,256 | 1/1970 | Kapalko et al. | 260/33.6 R |
| 3,911,134 | 10/1975 | Pommer et al. | 424/274 |

FOREIGN PATENT DOCUMENTS

| | | |
|---|---|---|
| 10635 | 10/1979 | European Pat. Off. . |
| 1238139 | 4/1967 | Fed. Rep. of Germany . |
| 265330 | 6/1978 | Fed. Rep. of Germany . |
| 1310083 | 10/1962 | France . |
| 2355451 | 1/1978 | France . |

*Primary Examiner*—Lorenzo B. Hayes
*Attorney, Agent, or Firm*—Schwartz, Jeffery, Schwaab, Mack, Blumenthal & Koch

[57] ABSTRACT

Disclosed is a composition and method for preserving wood and construction materials made of wood. The composition comprises more than about 65% by weight of at least one difficulty volatile organic-chemical solvent having a flash point higher than about 30° C. and of between about 0.35% by weight and 10.0% by weight of a specific fungicidal agent which is soluble, or at least partly soluble, in the organic-chemical solvent. The specific fungicidal agent is a mixture of N,N-dimethyl-N'-phenyl-N'-(fluoro dichloro methylthio) sulfamide and N,N-dimethyl-N'-(p-tolyl)-N'-(fluoro dichloro methylthio) sulfamide, in the proportion, by weight, of between about 25:10 and 10:30 and preferably between about 15:10 and 10:15. If desired, between about 0.1% by weight and 7.0% by weight of a soluble insecticidal agent may be added to the composition.

18 Claims, No Drawings

WOOD PRESERVING COMPOSITION AND METHOD OF USING SAME

BACKGROUND OF THE INVENTION

The present invention relates to an advantageous and highly effective method of preserving wood and construction materials made of wood, to preserving compositions used for said method, and to wood and materials made of wood preserved by means of such compositions, and more particularly to highly advantageous preserving compositions containing specific fungicides or mixtures of specific fungicides, and, if desired, also specific insecticides, dissolved in a difficultly volatile organic-chemical solvent or solvent mixtures of a specific flash point.

It is known to use N,N-dimethyl-N'-phenyl-N'-(fluoro dichloro methylthio) sulfamide as a fungicidal agent for preserving wood. See the journal "Holz als Roh- und Werkstoff," Vol. 25 (1977), pages 233 to 237. However, when using said, N,N-dimethyl-N'-phenyl-N'-(fluoro dichloro methylthio) sulfamide, there are encountered, among others, the disadvantages that, on the one hand, this compound dissolves difficultly or only slightly in the conventional formulation in aliphatic and aromatic organic solvents, whereas, in comparison with some other active compounds, higher concentrations of this compound are required in order to achieve a satisfactory fungicidal effect on the treated wood. On the other hand, another disadvantage of the above mentioned sulfamide is that this compound, after it has been applied to the wood, can partly crystallize on the surface of the wood in the form of fine, white crystals. Such blooming of the fungicidal agent N,N-dimethyl-N'-phenyl-N'-(fluoro dichloro methylthio) sulfamide ought to be prevented because it causes a loss in effectiveness and renders the wood surface unattractive.

Furthermore, the use of N,N-dimethyl-N'-(p-tolyl)-N'-(fluoro dichloro methylthio) sulfamide as a fungicidal agent and especially as a plant protective agent, is known. N,N-Dimethyl-N'-(p-tolyl)-N'-(fluoro dichloro methylthio) sulfamide has the advantage over N,N-dimethyl-N'-phenyl-N'-(fluoro dichloro methylthio) sulfamide that it is somewhat better soluble in certain organic solvents than the latter compound. However, when using N,N-dimethyl-N'-(p-tolyl)-N'-(fluoro dichloro methylthio) sulfamide dissolved in conventional solvents as a wood preserving agent, there can also occur formation of crystals or blooming of N,N-dimethyl-N'-(p-tolyl)-N'-(fluoro dichloro methylthio) sulfamide on the surface of the wood, especially at concentrations of the active agent exceeding 1%. Such formation of crystals and blooming on the wood surface renders the appearance of the wood quite unattractive and, furthermore, causes some loss of fungicidal agent within the wood.

If in a wood preserving composition one employs as the fungicidal agent either N,N-dimethyl-N'-phenyl-N'-(fluoro dichloro methylthio) sulfamide or N,N-dimethyl-N'-(p-tolyl)-N'-(fluoro dichloro methylthio) sulfamide and a binding agent which is soluble in the solvent used, for instance, an alkyd resin or linseed oil, upon applying such a wood preserving coating composition, and more particularly, as a wood preserving glazing or impregnating undercoating composition, there frequently is observed formation of a whitish incrustation of N,N-dimethyl-N'-phenyl-N'-(fluoro dichloro methylthio) sulfamide or N,N-dimethyl-N'-(p-tolyl)-N'-(fluoro dichloro methylthio) sulfamide on the surface of the coating or a milky turbidity in the coating itself. Sometimes this phenomenon may be observed only after several weeks or even months. It results, on the one hand, in a decrease of the effectiveness of the wood preserving composition and, more particularly, in a decrease in the effectiveness of the fungicidal agent contained therein, and, on the other hand, in an impairment of the surface of the coating or of the wood treated therewith. Due to this, the decorative effect of the treated wood surface is considerably diminished. The resulting bloomings, turbidities, and the like, can be removed by washing, but only with great difficulty. When attempting to rub them off, they are frequently spread over the whole surface of the treated wood (most probably due to the formation of crystal nuclei). Thus, any attempt to rub off the crystalline deposits can frequently even cause an intensification of the "blooming effect."

This "blooming effect" is especially encountered when applying preparations of N,N-dimethyl-N'-phenyl-N'-(fluoro dichloro methylthio) sulfamide and/or N,N-dimethyl-N'-(p-tolyl)-N'-(fluoro dichloro methylthio) sulfamide having a concentration exceeding 1% (calculated based on the wood preservation composition). These disadvantageous effects, however, can be observed also at lower concentrations, i.e., at concentrations below 1% of N,N-dimethyl-N'-phenyl-N'-(fluoro dichloro methylthio) sulfamide and/or N,N-dimethyl-N'-(p-tolyl)-N'-(fluoro dichloro methylthio) sulfamide, depending upon the composition of the wood preservative, the solvents employed, the temperature at which the preparations are applied and used, the kind of wood to be treated, and the like.

Many fungicidal agents used in preparing wood preserving compositions cannot be stored for a prolonged period of time or partly lose their effectiveness when used in combination with synthetic resins or certain solvents, or during drying of the coatings applied to the wood or materials made of wood. It would be advantageous to be able to use wood preserving compositions which contain as the fungicidal agents, two of the most effective fungicides, namely, N,N-dimethyl-N'-phenyl-N'-(fluoro dichloro methylthio) sulfamide and/or N,N-dimethyl-N'-(-tolyl)-N'-(fluoro dichloro methylthio) sulfamide. These fungicides do not exhibit the aforesaid disadvantages, such as instability on storage and are, according to available test data, essentially unobjectionable from a hygienic standpoint.

SUMMARY OF THE INVENTION

It is one object of the present invention to provide a composition useful for preserving wood and materials made of wood, which preparation contains as an active fungicidal and preserving agent N,N-dimethyl-N-aryl-N'-(fluoro dichloro methylthio) sulfamide and/or N,N-dimethyl-N'-(aryl alkyl)-N'-(fluoro dichloro methylthio) sulfamide, but which does not exhibit the disadvantages of the known wood preservative preparations as they have been pointed out hereinabove, more particularly, the disadvantages of crystal formation and of the decrease in effectiveness resulting therefrom as well as of the unattractive appearance of the surface of the treated wood resulting therefrom.

Another object of the present invention is to provide an effective method of treating wood and materials made of wood with such an advantageous and effective preserving composition.

Still another object of the present invention is to provide wood and materials made of wood which have been treated with a preserving composition according to the present invention.

In accomplishing these and other objects, there has been provided in accordance with the present invention a composition for preserving wood and construction materials of wood, comprising at least about 65% by weight and preferably at least about 72% by weight of a difficultly volatile organic-chemical solvent having a flash point higher than about 30° C.; and between about 0.35% by weight and about 10% by weight, preferably between about 1% and 7% by weight of at least one fungicidal agent which is at least partly soluble in the organic-chemical solvent, this fungicidal agent comprising a mixture of N,N-dimethyl-N'-phenyl-N;-(fluoro dichloro methylthio) sulfamide and N,N-dimethyl-N'-(p-tolyl)-N'-(fluoro dichloro methylthio) sulfamide in the relative proportion, by weight, of between about 25:10 and about 10:30, preferably between about 15:10 and 10:15. Optionally, the composition may further comprise between about 0.1% by weight and about 7.0% by weight, preferably between about 0.3 and 3% by weight of at least one insecticidal agent which is soluble in the organic-chemical solvent. The composition may also contain up up to about 65% by weight of the total fungicidal agent of a fungicidal agent in addition to those named above.

In accordance with another aspect of the present invention, there has been provided a method for preserving wood and construction material made of wood, comprising the steps of treating the wood and construction material made of wood with a preserving composition as defined above.

Other objects, features and advantages of the present invention will become apparent from the detailed description of preferred embodiments which follows.

DETAILED DESCRIPTION OF PREFERRED EMBODIMENTS

As is evident, the active fungicides N,N-dimethyl-N'-phenyl-N'-(fluoro dichloro methylthio) sulfamide and N,N'-dimethyl-N'-(p-tolyl)-N'-(fluoro dichloro methylthio) sulfamide differ in their structure merely by a methyl group. Therefore, it had to be assumed that these fungicides could form mixed crystals. Formation of such mixed crystals should not improve the solubility of the combination of these compounds in the composition according to the present invention. Therefore, it was highly surprising to find that, in contrast to this assumption, no blooming effects are observed when using the fungicides in the above-mentioned mixing proportions and proportions by weight of the fungicidal agents in the wood preserving compositions, or that even under unfavorable conditions, only a very considerably reduced formation of crystals occurs on the surface of the treated wood. The wood preserving compositions of the present invention which are prepared in the above-mentioned proportions, by weight, based on the given combinations of the fungicidal agents, can advantageously be used even if their content of softening agent or plasticizer, organic-chemical binding or bonding agent, or fixing or hardening agent in the composition is quite low.

According to a preferred embodiment of the present invention, between 0.5% by weight and 23% by weight and preferably between 2% by weight and 15% by weight of the difficultly volatile organic solvent or solvent mixture of a flash point higher than 30° C. can be replaced by the same amount of one or more organic-chemical binding or bonding agents, and/or fixing or hardening agents. In this case, there are added such binding or bonding agents and/or fixing or hardening agents which can readily be dispersed throughout the organic-chemical solvent or solvent mixture or which can be emulsified therein. Of course, the preferred additives of this type are those which are soluble in said solvents. Care must be taken, however, that the solvent or solvent mixture is partly replaced by said agents in such a manner that the resulting mixture or solvent mixture also has a flash point higher than 30° C. and that the organic-chemical solvent or solvent mixture is an oily or oil-like solvent.

According to another advantageous and preferred embodiment of the present invention, between 0.05% by weight and 6% by weight, and preferably between 0.1% by weight and 4% by weight of the difficultly volatile organic solvent or solvent mixture, preferably of the oily or oil-like solvent or solvent mixture can be replaced by the same amount of one or more oil-soluble dyestuffs which are soluble in the difficultly volatile solvent or solvent mixture. Other agents for replacing part of said solvent or solvent mixture are bitumen and/or inorganic coloring pigments which are insoluble in water and/or in the difficultly volatile organic solvent or solvent mixture, and/or organic coloring pigments which are also insoluble in water and/or the difficultly volatile organic solvent or solvent mixture. According to this embodiment of the present invention, there can be obtained colored wood preserving paints or transparent varnishes.

According to another embodiment of the present invention, between 0.1% by weight and 6% by weight, and preferably between 0.5% by weight and 3% by weight of the difficultly volatile, oily or oil-like organic-chemical solvent with a flash point higher than 30° C. is replaced by the same amount of an organic-chemical solvent or solvent mixture which is volatile at a low or medium-range temperature, which solvent or solvent mixture is soluble in said difficultly volatile oily or oil-like solvent provided that the resulting mixture or the resulting solvent mixture also has a flash point higher than 30° C. Preferably, hydrophilic solvents are used for this purpose, such as aliphatic and/or aromatic alcohols, ketones, alkyl glycol ethers, or alkyl glycol esters.

In accordance with still another embodiment of the present invention, up to 65% by weight and preferably up to 40% by weight of the N,N-dimethyl-N'-phenyl-N'-(fluoro dichloro methylthio) sulfamide and of the N-N-dimethyl-N'-(p-tolyl)-N'-(fluoro dichloro methylthio) sulfamide, said amount being calculated for the total amount of the mixture of said fungicidal agents, can be replaced by one or more other organic fungicides which are soluble in the organic-chemical solvent.

Suitable fungicidal agents which can be used and added to the mixture of fungicides according to the present invention are, for instance, (a) fungicidal oil-soluble naphthenates, preferably zinc and/or copper naphthenates;

(b) 8-hydroxy quinoline or its fungicidal oil-soluble salts or derivatives, preferably phenyl mercury-8-hydroxy quinolate;

(c) fungicidal compounds or derivatives or, respectively, mixtures of chloro-phenols, preferably compounds or mixtures of penta- and/or tetra-chlorophenols with difficultly volatile amines, for instance, rosin amine;

(d) nitro-phenols or nitro-chloro-phenols and/or nitro-chloro-benzenes, especially 1,2-dinitro-tetrachlorobenzenes and/or benzimidazole-2-carbamide acid methyl ester and/or oil-soluble fungicidal metal-containing organic compounds, for instance, of zinc, copper, manganese, cobalt, chromium, or mercury, such as, for instance, the corresponding caprylates, naphthenates, oleates, and the like; or (e) fungicidal salts of the N-nitroso-N-cyclohexyl hydroxylamine, preferably the aluminum salt of the N-nitroso-N-cyclohexyl hydroxylamine, and/or N-trichloro methylthio tetrahydrophthalimide.

Other fungicidal agents which can be added are oil-soluble tetravalent fungicidal organo-tin compounds, for instance, bis-(tributyl tin) oxide, tri-n-butyl tin trichloro acetate, tri-n-butyl tin-8-hydroxy quinoline, tri-n-butyl tin pentachloro phenol, tri-n-butyl tin bis-ethylenedithiocarbamate, tri-n-butyl tin benzoyl cyano acetic acid, tri-n-butyl tin fluoride, tri-n-butyl tin thiocyanate, tributyl tin dichloro phenolate, and also the adduct tri-n-butyl tin acrylate/hexachloro cyclopentadiene. Combinations of the mixture of fungicidal agents according to the present invention with zinc propylene-1,2-bis-dithiocarbamidate, dimethyl-(2,2,2-trichloro-1-hydroxy ethyl) phosphonate, O,O-dimethyl-S-(4-oxo-1,2,3-benzotriazin-3(4H)-yl methyl) phosphordithiate, O,O-diethyl-O-p-nitro phenyl phosphoro thioate, and-/or 6-methyl-2,3-quinoxaline have proved to be highly effective.

Furthermore, the mixture of fungicidal agents can be used in combination with

N-(1,1,2,2-tetrachloro-2-fluoro-ethylthio) methane sulfonic acid anilide,
1,1-dimethyl-3-(3,4-dichloro phenyl) urea,
tetramethyl thiouram disulfide, and/or
N-cyclohexyl-N-methoxy-2,5-dimethyl-3-furamide.

Furthermore, there can be employed the mixture of the fungicidal agents of the present invention in combination with
organic phosphoric acid esters of the formula

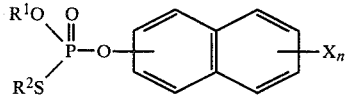

in which
R$^1$ indicates alkyl with 1 to 4 carbon atoms,
R$^2$ indicates a saturated or unsaturated alkyl group with 1 to 4 carbon atoms, or
a group of the formula

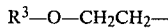

in which
R$^3$ indicates alkyl with 1 to 4 carbon atoms,
X indicates hydrogen or halogen, and
n indicates one of the numerals 1, 2, or 3; and/or
N-(dimethylamino methylidene) thiol (thiono) phosphoric acid ester imides of the following formula

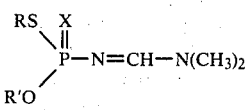

in which
X indicates an oxygen atom or a sulfur atom,
R' indicates alkyl with 1 to 6 carbon atoms, and
R indicates alkyl, alkenyl, alkinyl, aralkyl, alkyl thioalkyl or alkenyl thioalkyl; and or
5-imino-1,2,4-triazine derivatives of the following formula

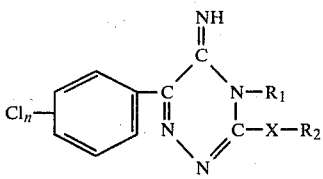

in which
n indicates one of the numerals 0 or 1,
R$_1$ indicates alkyl with 1 to 4 carbon atoms, or the amino group,
R$_2$ indicates alkyl with 1 to 4 carbon atoms, and
X indicates oxygen, sulfur, or the amino group —NH—.

As hydrophilic solvents there are preferably used such solvents which have a flash point higher than 30° C. and a vaporization number higher than 35. Preferably, there are used corresponding aliphatic and/or aromatic alcohols, ketones, alkyl glycol ethers, and/or alkyl glycol esters, for instance, alkyl glycol acetate.

As stated above, the present invention relates, furthermore, to a method of preserving wood and construction materials made of wood. Said method comprises the treatment of wood or construction materials made of wood with an advantageous and highly effective wood preserving preparation of a specific composition. According to the present invention the composition consists of more than 65% by weight and preferably more than 72% by weight of at least one difficultly volatile organic-chemical solvent, said solvent having a flash point higher than 30° C. The composition contains, furthermore, between 0.35% by weight and 10% by weight, and preferably between 1% by weight and 7% by weight of at least one specific fungicidal agent which is soluble, or partly soluble in said difficultly volatile organic-chemical solvent with a flash point higher than 30° C. If desired, there can be added to said composition between 0.1% by weight and 7% by weight, and preferably between 0.3% by weight and 3% by weight of at least one insecticidal agent, which is soluble in said difficultly volatile organic-chemical solvent with a flash point higher than 30° C. In connection with this method according to the present invention, there is used as fungicidal agent a mixture of an N,N-dimethyl-N'-aryl-N'-(fluoro dichloro methylthio) sulfamide and, more particularly, N,N-dimethyl-N'-phenyl-N'-(fluoro dichloro methylthio) sulfamide, and of an N,N-dimethyl-N'-aralkyl-N'-(fluoro dichloro methylthio) sulfamide and, more particularly, N,N-dimethyl-N'-(p-tolyl)-N'-(fluoro dichloro methylthio) sulfamide. The mixtures of these agents are used in specific proportions by weight, namely, in the proportion between 25:10 and 10:30 and preferably in the proportion between 15:10 and 10:15 of N,N-dimethyl-N'-phenyl-N'-(fluoro dichloro methylthio) sulfamide to N,N-dimethyl-N'-(p-tolyl)-N'-(fluoro dichloro methylthio) sulfamide. The wood-preserving composition according to the present invention is prepared by treating the above-mentioned fungicidal agents in the difficultly volatile organic-chemical solvent of a flash point higher than 30° C. at a temperature between −5° C. and +80° C. and preferably at a temperature between +20° C. and +40° C. and at a pressure between 400 mm. Hg and 850 mm. Hg until a clear solution or a dispersion of a clear appearance is obtained. The pressure is preferably between 650 mm. Hg and 790 mm. Hg.

The following examples serve to illustrate the present invention without, however, limiting the same thereto.

EXAMPLE 1

Wood preserving surface-coating composition with fungicidal insecticidal, and anti-blue rot activity. The composition consists of:

| | |
|---|---|
| N,N-Dimethyl-N'-phenyl-N'-(fluoro dichloro methylthio) sulfamide | 1.0% |
| N,N-dimethyl-N'-(p-tolyl)-N'-(fluoro dichloro methylthio) sulfamide | 1.0% |
| "Lindane" (hexachloro cyclohexane) | 0.5% |
| linseed oil varnish | 15.0% |
| alkyd resin solution (60%) | 5.0% |
| siccative | 0.2% |
| aromatic solvents (boiling range: 180–210° C.) | 77.3% |

EXAMPLE 2

Wood preserving impregnating composition with fungicidal insecticidal, and anti-blue rot activity. The composition consists of:

| | |
|---|---|
| "Lindane" | 0.5% |
| N,N-dimethyl-N'-phenyl-N'-(fluoro dichloro methylthio) sulfamide | 0.7% |
| N,N-dimethyl-N'-(p-tolyl)-N'-(fluoro dichloro methylthio) sulfamide | 1.0% |
| dibutyl phthalate | 6.0% |
| tributyl phosphate | 2.0% |
| aromatic solvents (boiling range: 180–210° C.) | 39.8% |
| mineral spirits (boiling range: 180–210° C.) | 40.0% |

EXAMPLE 3

Preservative composition with fungicidal and anti-blue rot activity. The composition consists of:

| | |
|---|---|
| "Lindane" | 1.0% |
| N,N-dimethyl-N'-phenyl-N'-(fluoro dichloro methylthio) sulfamide | 0.6% |
| N,N-dimethyl-N'-(p-tolyl)-N'-(fluoro dichloro methylthio) sulfamide | 1.2% |
| dibutyl phthalate | 8.0% |
| aromatic solvents (boiling range: 180–210° C.) | 89.2% |

EXAMPLE 4

Anti-blue rot impregnating and surface coating (priming) composition with insecticidal activity. The composition consists of:

| | |
|---|---|
| Alkyd resin solution (60%) | 10.0% |
| N,N-dimethyl-N'-phenyl-N'-(fluoro dichloro methylthio) sulfamide | 0.3% |
| N,N-dimethyl-N'-(p-tolyl)-N'-(fluoro dichloro methylthio) sulfamide | 0.4% |
| "Lindane" | 0.5% |
| aromatic solvents | 88.6% |
| drying agent | 0.2% |

EXAMPLE 5

Anti-blue rot impregnating composition with fungicidal and insecticidal activity. The composition consists of:

| | |
|---|---|
| N,N-dimethyl-N'-phenyl-N'-(fluoro dichloro methylthio) sulfamide | 0.8% |
| N,N-dimethyl-N'-(p-tolyl)-N'-fluoro dichloro methylthio) sulfamide | 0.9% |
| persulfone | 0.3% |
| "Lindane" | 0.5% |
| dibutyl phthalate | 6.0% |
| tributyl phosphate | 2.0% |
| aromatic solvents | 89.5% |

EXAMPLE 6

Wood-protective composition with anti-blue rot fungicidal and insecticidal activity. The composition consists of:

| | |
|---|---|
| N,N-dimethyl-N'-phenyl-N'-(fluoro dichloro methylthio) sulfamide | 0.9% |
| N,N-dimethyl-N'-(p-tolyl)-N'-(fluoro dichloro methylthio) sulfamide | 0.9% |
| "Lindane" | 0.5% |
| alkyd resin (100%) | 20.0% |
| pigments (iron oxide, carbon black, and others) | 2.0% |
| siccative | 0.2% |
| wetting agent, skin protective agent | 0.3% |
| aromatic hydrocarbons | 50.0% |
| mineral spirits | 25.2% |

EXAMPLE 7

Concentrated wood preserving composition. The concentrated composition is composed of:

| | |
|---|---|
| N,N-dimethyl-N'-phenyl-N'-(fluoro dichloro methylthio) sulfamide | 2.4% |
| N,N-dimethyl-N'-(p-tolyl)-N'-(fluoro dichloro methylthio) sulfamide | 2.7% |
| "Lindane" | 1.5% |
| dibutyl phthalate | 18.0% |
| tributyl phosphate | 6.0% |
| aromatic solvents (boiling range: 180–210° C.) | 69.4% |

The concentrated composition is used for producing an impregnating solution with preventive fungicidal, insecticidal, and anti-blue rot activity.

Such an impregnating solution is prepared by diluting the concentrated composition with aliphatic and aromatic solvents in the proportion of 1:2.

As stated hereinabove, the compositions described in Examples 1 to 7 are prepared by adding the various agents and compounds to the solvents at a temperature between 25° C. and 40° C. and stirring the mixture until a clear solution or a dispersion of a clear appearance is obtained.

Of course, many changes and variations in the composition of the wood preserving compositions according to the present invention, the difficultly volatile organic-chemical solvents with a flash point higher than 30° C., the insecticides and anti-blue rot agents added to the solvents used, as well as the other additives employed, such as siccatives, pigments, binding or bonding agents, fixing or hardening agents, alkyd resins, wetting agents, and the like additives, the proportion of the active fungicidal agents in the composition, the method of producing the wood-protective compositions, and the like, may be made by those skilled in the art in accordance with the principles set forth herein, without departing from the spirit and scope of the present invention.

What is claimed is:

1. A composition for preserving wood and construction materials of wood, said composition comprising:
   at least about 65% by weight of a difficultly volatile organic-chemical solvent having a flash point higher than about 30° C.; and
   between about 0.35% by weight and about 10% by weight, of a fungicidal agent which is at least partly soluble in said organic-chemical solvent, said fungicidal agent comprising a mixture of N,N-dimethyl-N'-phenyl-N'-(fluoro dichloro methylthio) sulfamide and N,N-dimethyl-N'-(-p-tolyl)-N'-(fluoro dichloro methylthio) sulfamide in the relative proportion, by weight, of between about 25:10 and about 10:30.

2. A composition according to claim 1, wherein said organic-chemical solvent comprises at least about 72% by weight of the composition.

3. A composition according to claim 1 or 2, wherein said fungicidal agent comprises between about 1.0% by weight and about 7% by weight of the composition.

4. A composition according to claim 1, wherein the N,N-dimethyl-N'-phenyl-N'-(fluoro dichloro methylthio) sulfamide and the N,N-dimethyl-N'-(p-tolyl)-N'-(fluoro dichloro methylthio) sulfamide are present in the mixture of fungicidal agents in the relative proportion, by weight of between about 15:10 and about 10:15.

5. A composition according to claim 1, further comprising between about 0.1% by weight and about 7.0% by weight of at least one insecticidal agent which is soluble in said organic-chemical solvent.

6. A composition according to claim 5, wherein said insecticidal agent is present in an amount between about 0.3% by weight and about 3.0% by weight of the composition.

7. A composition according to claim 1, wherein between about 0.5% by weight and about 23% by weight of said organic-chemical solvent is replaced by the same amount of at least one additive selected from the group consisting of an organic-chemical binding or bonding agent, a fixing or hardening agent, and mixtures thereof, said additives being at least dispersible in said organic-chemical solvent, the mixture of said solvent and said additives also having a flash point higher than about 30° C., said organic-chemical solvent being an oily or oil-like solvent.

8. A composition according to claim 7, wherein between about 2.0% by weight and about 15.0% by weight of said organic-chemical solvent is replaced by said additives.

9. A composition according to claim 1, wherein between about 0.05% by weight and about 6.0% by weight of said organic-chemical solvent is replaced by the same amount of at least one coloring material selected from the group consisting of an oil-soluble dyestuff which is soluble in said organic-chemical solvent, bitumen, inorganic and organic pigments which are insoluble in water or acid organic-chemical solvent and mixtures of said coloring materials.

10. A composition according to claim 9, wherein between about 0.1% by weight and about 4.0% by weight of said organic-chemical solvent is replaced by said coloring material.

11. A composition according to claim 1, wherein said organic-chemical solvent comprises a first oily or oil-like solvent, and between about 0.1% by weight and about 6.0% by weight of said first organic-chemical solvent is replaced by the same amount of a second organic-chemical solvent of medium high or high volatility, said second solvent being soluble in said first solvent, and said mixture of solvents also having a flash point higher than about 30° C.

12. A composition according to claim 11, wherein between about 0.5% by weight and about 3.0% by weight of said first solvent is replaced by the same amount of said second solvent.

13. A composition according to claim 1, wherein up to 65% by weight of said fungicidal agent comprises at least one additional organic fungicidal agent which is soluble in said organic-chemical solvent.

14. A composition according to claim 13, wherein said additional fungicidal agent comprises up to 40% by weight of the total fungicidal agent.

15. A method for preserving wood and construction material made of wood, comprising the steps of treating the wood and construction material made of wood with a preserving composition as defined by claim 1.

16. A method according to claim 15, in which said organic-chemical solvent is present in the wood preserving composition in an amount exceeding about 72% by weight of the composition, the mixture of fungicidal agents is present in an amount between about 1.0% by weight and about 7.0% by weight and the fungicidal agents N,N-dimethyl-N'-phenyl-N'-(fluoro dichloro methylthio) sulfamide and N,N-dimethyl-N'-(p-tolyl)-N'-(fluoro dichloro methylthio) sulfamide are present in the composition in the proportion by weight, of between about 15:10 and about 10:15.

17. A method according to claim 15, wherein the wood preserving composition further comprises between about 0.1% by weight and about 7.0% by weight of at least one insecticidal agent which is soluble in said organic-chemical solvent.

18. A method according to claim 17, in which the insecticidal agent is added to the composition in an amount between about 0.3% by weight and about 3.0% by weight.

* * * * *